United States Patent [19]

Chang

[11] Patent Number: 6,106,835
[45] Date of Patent: *Aug. 22, 2000

[54] **MODIFIED BINDING MOLECULES SPECIFIC FOR T OR B LYMPHOCYTES AND THEIR USE AS *IN VIVO* IMMUNE MODULATORS**

[75] Inventor: Tse Wen Chang, Houston, Tex.

[73] Assignee: Tanox, Inc., Houston, Tex.

[*] Notice: This patent is subject to a terminal disclaimer.

[21] Appl. No.: 08/011,130

[22] Filed: Jan. 28, 1993

Related U.S. Application Data

[63] Continuation-in-part of application No. 07/926,566, Aug. 6, 1992, abandoned, which is a continuation of application No. 07/688,000, Apr. 19, 1991, abandoned.

[51] Int. Cl.$^7$ ..................................................... A61K 39/40
[52] U.S. Cl. .................................... 424/178.1; 530/391.1; 530/388.75; 530/389.6; 530/387.1
[58] Field of Search ........................... 530/391.1, 388.75, 530/389.6, 387.1; 424/85.8, 480, 178.1

[56] References Cited

U.S. PATENT DOCUMENTS

| | | | |
|---|---|---|---|
| 4,867,973 | 9/1989 | Goers et al. | 424/85.91 |
| 4,925,648 | 5/1990 | Hansen et al. | 530/402 |
| 5,024,940 | 6/1991 | Brenner et al. | 530/387 |

FOREIGN PATENT DOCUMENTS

| | | |
|---|---|---|
| 3242389 | 5/1989 | Australia . |
| 6623590 | 5/1991 | Australia . |
| 0336379 | 4/1989 | European Pat. Off. . |
| WO8912458 | 12/1989 | WIPO . |
| WO9006758 | 6/1990 | WIPO . |
| WO9013281 | 11/1990 | WIPO . |
| WO9013316 | 11/1990 | WIPO . |
| WO9103493 | 3/1991 | WIPO . |
| WO9206193 | 4/1992 | WIPO . |
| WO9207878 | 5/1992 | WIPO . |
| WO9213562 | 8/1992 | WIPO . |

OTHER PUBLICATIONS

Williams, J.M. et al. J. of Immunol. 135:2249–2255 (1985).
Geppert, T.D. et al. J. of Immunol. 138:1660–1666 (1987).
Ceuppens, J.L. et al. J. of Immunol. 137:1816–1821 (1986).
Rodwell, J.D. et al. Proc. Natl. Acad. Sci. USA 83:2632–2636 (1986).
Brunswick et al. J. Immunol. 140:3364–72 (1988).
Blazer et al. J. Immunol. 147:1492–1503 (1991).
Hirsch et al J. Immunol. 147:2088–93 (1991).
Ellenhorn, J.D.I. Transplantation 50:608–612 (1990).
Richards, J.M. New Engl. Journal. of Med. 323:487 (1990).
Osband, M.E. et al. The Lancet 335:494–498 (1990).
Leo, O. et al. Proc. Natl. Acad. Sci. USA 84:1374–1378 (1987).
Hirsch, R. et al. J. of Immunol. 142:737–743 (1989).
Hirsch, R. et al. Transplantation 47:853–857 (1989).
Hirsch, R. et al. Transplantation 49:1117–1123 (1990).
Hirsch, R. et al. The Lancet (1989).
Kast, W.M. et al. J. of Immunol. 145:2254–2259 (1990).
Ellenhorn, J.D.I. et al. J. of Immunol. 144:2840–2846 (1990).
Ellenhorn, J.D.I. et al. Science 242:569–571 (1988).
Nayersina et al. Abstract from Mechanisms of Tumor Rejection II A1713 #7793 (1991).
Baniyash, M. et al. J. Biological Chem. 263:9874–9878 (1988).
Geisler, C. et al. J. of Immunol. 145:1761–1767 (1990).
Bravehamp et al Anal Biochem 131:25–33 1983.
Huang et al J Biol Chem 1983.
Raith *Immunology* Gower Medical Publishing 1985 p. 8.7 Fig 8.19.
Williams et al J Immunology 135(4):2249–2255 1985.
Geppert et al J Immunology 138(6):1660–1666 1987.
Verwilghen et al Immunology 72:269–276 1991.
Harris et al TioTech 11:42–46 1993.
Waldmann Science 252:1657–1662 1991.
Hanlow et al Antibodies A Laboratory Manual (1988) Col Spring Hanbon Press p. 626.
Martin et al 136:3282–3287 (1986).
Osband et al Immunology Today 11:193–195 (1990).
Paul *Fundamental Immunology* Raven Press (1989) p. 364.
Webster's II New Riverside University Dictionary (1988) pp. 738 & 880.

*Primary Examiner*—Keith D. MacMillan
*Assistant Examiner*—T. D. Wessendorf
*Attorney, Agent, or Firm*—Eric P. Mirabel

[57] ABSTRACT

Several forms of immunoregulatory substances are derived from monoclonal antibodies (MAbs) that are specific for a T or B cell surface antigen, such as CD3, TCR, CD4, or CD8 on T cells or membrane-bound immunoglobulins on B cells. The substances include: a mixture of F(ab')$_2$ fragments (or other divalent binding molecules which lack Fc) which each bind noncompetitively to different monovalent antigenic epitopes on the same antigen; the F(ab')$_2$ fragment (or other divalent binding molecules which lack Fc) of a bispecific antibody which has each of its binding sites derived from one of the two MAbs that bind noncompetitively to monovalent antigenic epitopes on the same antigen; a conjugate including a polymeric backbone, such as polyethylene glycol ("PEG"), cellulose, dextran, agarose, or an amino acid copolymer or a liposome, that is coupled with the binding molecules, e.g., Fv, Fab, or F(ab')$_2$, which bind noncompetitively to monovalent antigenic epitopes on the same antigen.

8 Claims, 4 Drawing Sheets

MODIFIED BINDING MOLECULES SPECIFIC FOR T OR B LYMPHOCYTES AND THEIR USE AS *IN VIVO* IMMUNE MODULATORS

This is a continuation-in-part of application Ser. No. 07/926,566, filed on Aug. 6, 1992 (abandoned), which is a continuation of application Ser. No. 07/688,000, filed on Apr. 19, 1991 (abandoned).

FIELD OF THE INVENTION

The invention relates to binding molecules, such as antibody fragments and inmunoconjugates, for modulating the immune system by inducing specifically the polyclonal activation, proliferation, and/or lymphokine production of T or B lymphocytes, or subsets thereof.

BACKGROUND OF THE INVENTION

Most immune responses involve many components of the immune system. Although the immune mechanisms involved in the elimination of malignantly transformed cells are not well understood, it is reasonable to assume that if more immune mechanisms are activated and enhanced, the tumorous cells may be eliminated more effectively. Also, both humoral and cellular mechanisms are known to be involved in the immune response against viruses and virus-infected cells. Thus, generally speaking, for the therapeutic treatments of patients with various cancers or infectious diseases, and for protecting individuals exposed to infectious agents from contracting the infection, it is desirable to enhance the entire immune system.

The various branches of the immune system include antibodies, cytotoxic T cells (CTLs), T cells mediating delayed-type hypersensitivities ($T_{TDH}$ cells), monocytes and macrophages, natural killer cells, K cells mediating ADCC, and granulocytes. Complex interactions are involved in the activation of these various branches. The helper T cells ($T_h$ cells) play central regulatory roles, and many factors are secreted by these cells and other cells in a certain concerted fashion during the activation and proliferation phases. There is good reason to believe that the concerted production of lymphokines and cytokines, at the appropriate time and in the proper relative proportions, is important for maximizing the immune response.

Potentiation of the immune system is desirable for treating a number of pathologic conditions, e.g., for treatment of malignant tumors. The immune potentiators include substances identified from screening natural sources, such as cultures of microorganisms, marine animals, herbs, or plants, as well as substances screened from large batteries of synthetic organic compounds.

One example of a substance from a natural source is muramyl dipeptide, which has been identified as the smallest structure from the cell wall of staphylococcal bacteria which still retains immune potentiating effects. Many analogues of muramyl dipeptide have been synthesized. Muramyl dipeptide and its analogues are macrophage activators, and have been tested and developed as therapeutic agents for tumors and as adjuvants for vaccines.

Other examples of immune potentiators derived from natural sources include double-stranded RNA and mismatched double-stranded RNA (also called ampligen) which can induce interferon synthesis and other immune functions. These substances have also been tested for treating tumors and viral diseases, such as AIDS.

Immune potentiators may be applied to patients alone or in combination with surgery, irradiation, or chemotherapy. They may also be desirable for treating patients with viral infectious diseases or for protecting individuals, after exposure to viruses, from contracting infection. Immune potentiators may be useful as adjuvants for various vaccines for infectious diseases or cancers.

Recently, recombinant human lymphokines and cytokines have been produced by genetic engineering. Many such recombinant "biological response modifiers" are being tested for treatment of various cancers and infectious diseases. A few recombinant products, such as interleukin-2 (IL-2), α-interferon, γ-interferon, granulocyte-colony stimulation factor and granulocyte/monocyte-colony stimulation factor (G-CSF, GM-CSF), have been approved in many countries for use against certain cancers and infectious diseases. For example, IL-2 is approved for treating patients with renal cell carcinoma; α-interferon is approved for treating patients with hairy cell carcinoma or with hepatitis B infection; G-CSF and GM-CSF are approved for treating cancer patients receiving chemotherapy for the purposes of restoring lost neutrophils.

Individual recombinant lymphokines, such as IL-2, IL-4, or γ-interferon can augment some aspects of the immune system, but function only against limited immunocyte targets and can only potentiate certain immune functions and not the entire immune system. They also probably function only over short ranges and in limited areas in vivo. Also, cytokines and lymphokines which are injected into patients are cleared rapidly through the kidneys. They likely will not be present in sufficiently high concentrations in the lymphoid system for long enough to achieve their desired immunological effects.

Of the various substances other than lymphokines or cytokines which have been studied for potentiating the immune system, most which are suitable for in vivo use do not target or enhance the T cells directly. For example, muramyl dipeptide, and analogues thereof, primarily activate macrophages. Double-stranded RNA and mismatched double-stranded RNA mainly induce interferon production by a variety of cells.

A few naturally-derived protein substances are known to be potent T cell mitogens in culture in vitro, and have been used in studies to characterize and quantitate T cell activity. These substances include phytohemagglutinin A (PHA), concanavalin A (Con A), wheat germ agglutinin (WGA), and some other lectins, defined as carbohydrate-binding plant proteins. However, these T-cell mitogenic proteins, although very useful for in vitro studies, have poor specificity and therefore bind to almost all cell types. Because they are toxic and lack specificity, they are not effective for in vivo use as T cell potentiators.

In order to activate and expand lymphocytes to achieve satisfactory therapeutic effects while avoiding administering toxic substances, some groups have sought to activate and expand the T lymphocytes from patients in culture in vitro for a period of time under optimal conditions and then harvest the activated cells and inject them back into the same patients. In this so-called IL-2/LAK therapeutic regimen, used by the Biological Therapy Institute (Franklin, Tenn.) to treat patients with various cancers, the blood is first drawn from the patients and the mononuclear cells are isolated. See Rosenberg, S. A. et al., *N. Eng. J. Med.* 316:889 (1987). The cells are incubated in medium containing recombinant IL-2 for several weeks, and the activated and expanded T cells, which contain the lymphokine-activated killer (LAK) cells, are harvested and injected into the patients.

A more recent, modified version of this IL-2/LAK therapy, known as autolymphocyte therapy (ALT) has been developed by Cellcor Therapies, Inc. in Boston, Mass. See Osband, M. E. et al., *Lancet* 335:994 (1990). The lymphocytes from renal cell carcinoma patients are taken twice. The first time, the lymphocytes are stimulated with antibodies specific for human CD3 antigen (anti-CD3) in vitro to produce lymphokines. The culture supernatant is collected after a few days of culturing, and the cells are discarded. The second time, the lymphocytes taken from the patients are incubated in the autologous lymphokines for a period of five days and the cells are harvested and injected into the same patients.

It is claimed that these approaches, involving in vitro lymphocyte stimulation and expansion, achieve beneficial responses in a portion of the treated patients. The major concern with these regimes is that the treatment is very tedious, expensive, and requires sophisticated, specialized cell culture facility. The variation among cells or cultures from different patients requires demanding monitoring procedures. Also, lymphocyte cultures have very poor viability even under optimal conditions, meaning that during the culturing, large numbers of the cells will die. When large numbers of dead cells are injected into patients, this may actually burden the reticuloendothelial system (RES) and reduce its effectiveness in combating the tumor cells.

In summary, the clinical studies and approved routine uses of IL-2 and γ-interferon and of LAK or ALT therapies indicate that T cell activation and expansion can achieve therapeutic effects in some patients with cancers or infectious diseases. On the other hand, the results of these treatments suggest that the lymphokine treatments have certain deficiencies and the LAK and ALT treatments have some substantial drawbacks. Thus, an efficacious and feasible treatment may be realized if these deficiencies can be eliminated.

A number of MAbs specific for CD3 on the surface of human T cells (pan T marker) are known to be very potent mitogens of human T cells in vitro, e.g., the MAb OKT3. Van Wauwe, J. P. et al., *J. Immunology* 124:2708 (1980); Chang, T. W. et al., *Proc. Natl. Acad. Sci. U.S.A.* 78:1805 (1981); MAb 64.1 Hansen, J. A. et al., *Leukocyte Typing: Human Leukocyte Differentiation Antigens Detected by Monoclonal Antibodies,* Eds. Bernard, A. et al. (Spring Verlag, N.Y. 1984). In medium containing only fetal calf serum and no human serum (and therefore no IgG), the anti-CD3 MAbs are much more potent than PHA or Con A in inducing T cell proliferation.

But the mitogenic effect of anti-CD3 requires both specific binding to the CD3 antigen and the presence of the Fc moiety of the antibody, as well as the presence of monocytes and macrophages. The best explanation for these results is that the Fc of the anti-CD3 MAbs binds to the Fc receptors on monocytes/macrophages, thereby aggregating the CD3 antigen on the T cell surface. Since CD3 is associated with the T cell antigen receptors, the aggregation of CD3 triggers the activation and proliferation of the T cells.

This explanation is supported by experiments which show that when the anti-human CD3 MAb is conjugated to Sepharose 4B beads or coated on the substratum plastic surface of culture wells, monocytes and macrophages are not needed to induce activation and proliferation of T cells. See Williams, J. M. et al., *J. Immunol.* 135:2249 (1985); Ceuppens, J. L. & Baroja, M. L., *J. Immunol.* 137:1816 (1986); Geppert, T. D. & Lipsky P. E., *J. Immunol.* 138:1660 (1987). Based on these experiments, it has been suggested that the solid-phase anti-CD3 MAb functions by aggregating the CD3 antigen on the T cell surface.

However, when anti-human CD3 is injected in vivo, the results are the opposite of the in vitro effects. OKT3 MAb, which is the first MAb ever approved for therapeutic use in vivo, is strongly immunosuppressive and is approved for use as an immunosuppressor for patients receiving kidney transplants. Ortho Multicenter Group Study, *N. Eng. J. Med.* 313:337 (1985). The injection of OKT3 causes rapid depletion of T cells from the circulation. Although the mechanism by which anti-CD3 causes this rapid depletion of T cells is not well understood, the best explanation is that anti-CD3 induces ADCC of the T cells, i.e., as the T cells coated by anti-CD3 circulate through the spleen and liver, they are lysed by the phagocytic cells of the RES in these organs. It is also possible that some of the T cells are destroyed by complement-mediated cytolysis and some other cytolytic mechanisms.

In in vivo mouse studies using a hamster MAb against murine CD3, it has been shown that low doses of anti-CD3 can prevent malignant progressive tumor growth and protect against lethal sendei virus infection. Ellenhorn, J. D. et al., *Science* 242:569 (1988); Kast, W. M. et al., *J. Immunol.* 145:2254 (1990). It has been suggested that the T cells in the mice are activated by such treatment with anti-CD3. Hirsch, R. et al., *J. Immunol.* 142:737 (1989).

Human and murine studies involving in vivo administration of anti-CD3 indicate that there is a substantial difference between the two species. In humans, even minute amounts of anti-CD3 are immunosuppressive and cytolytic. Also, the activation and mitogenic effect of anti-CD3 on T cells is completely blocked by the presence of human serum or IgG. Chang, T. W. et al., *Proc. Natl. Acad. Sci. U.S.A.* 78:1805 (1981); Looney, R. F. and Abraham, G. N. *J. Immunol.* 133:154 (1984). These results suggest that whole anti-CD3, or fragments thereof, will not activate T cells in humans in vivo, and therefore, the invention described below is not suggested.

SUMMARY OF THE INVENTION

The immunoregulatory substances of the invention include: a mixture of F(ab')$_2$ fragments (or other divalent binding molecules which lack Fc) which each bind noncompetitively to different monovalent antigenic epitopes on the same antigen; the F(ab')$_2$ fragment (or other divalent binding molecules which lack Fc) of a bispecific antibody which has each of its binding sites derived from one of the two MAbs that bind noncompetitively (i.e., without significant hindrance from each other) to monovalent antigenic epitopes on the same antigen; a conjugate including a polymeric backbone, such as polyethylene glycol ("PEG"), cellulose, dextran, agarose, or an amino acid copolymer or a liposome, that is coupled with binding molecules, e.g., Fv, Fab, or F(ab')$_2$, which bind noncompetitively to monovalent antigenic epitopes on the same antigen.

The immunoregulatory substances of the invention are specific for a surface antigen of T cells, or B cells, or a subset thereof. These antigens include: CD3, idiotype bearing receptor chains and other T cell receptor (TCR)-linked components; CD4, CD8, and other T cell-specific surface components; membrane-bound immunoglobulins of different isotypes on B cells. Many of these antigens contain only a single binding site for each MAb (i.e., a monovalent antigenic epitope).

The main use for the immunoregulatory substances is as immune potentiators, which activate and expand T or B cells or a subset of these cells, and stimulate them to produce IL-2, γ-interferon, IL-1, IL-4, IL-6, tumor necrosis factor (TNF), or other lymphokines. Because T cells play central roles in the regulation of many branches of the immune system, the concerted secretion of a number of lymphokines will activate many immune mechanisms, whereas the administration of individual lymphokines will have a more limited effect.

Such immune potentiators may be used to treat patients with cancers or infectious diseases, or to protect individuals exposed to infectious agents from contracting the infections. Immune potentiators may be applied as adjuvants for vaccines.

The selective stimulation of a T or B cell subset may also be desirable. For example, for stimulating antibody production in patients deficient of IgA and receiving vaccines, immune potentiators may be used to stimulate the production of IgA in the mucosal tissues. Such an immune potentiator may be a MAb fragment specific for the extracellular portion of the membrane anchor peptide of membrane-bound IgA ("mIgA"), as described in International Application No. PCT/US90/03532. This fragment binds to mIgA but not to secreted, circulating IgA.

Many of the antigens on T or B cells (or subsets thereof) contain only one antigenic epitope which is specific for one unique MAb. The one MAb fragment by itself cannot crosslink and aggregate the surface antigen, which is often required for cell activation. In contrast, the products of this invention are designed to cross-link and aggregate the surface antigens without triggering complement-mediated cytolysis or antibody-mediated cellular cytotoxicity (ADCC) in vivo.

In one embodiment, the invention includes $F(ab')_2$ fragments (and other divalent binding molecules lacking Fc) which accomplish these objectives. The first fragments of the invention (including $F(ab')_2$ and other divalent binding molecules) bind noncompetitively to monovalent antigenic epitopes on the same antigen. The second fragments of the invention (including $F(ab')_2$ and other fragments) are derived from a bispecific antibody which has each of its binding sites derived from one of the two MAbs that bind noncompetitively to monovalent antigenic epitopes on the same antigen.

In another embodiment, the invention includes a molecular backbone or base to which binding molecules (including Fv, Fab, and $F(ab')_2$) may be conjugated. The backbone may be PEG, cellulose, dextran, agarose or other hydrophilic polymers. Active groups for cross-linking may be introduced by established methods. Alternatively, long chain peptides containing Lys, or Cys residues may be synthesized. A preferred family of amino acid copolymers are synthesized by a routine method, containing Gly, Ser, and Lys (or Cys) at 20:4:1 ratio, with molecular weights of 10,000 to 1,000,000 (about 150 to 15,000 amino acid residues long). Liposomes may also be used as the base for conjugating antibody fragments.

DETAILED DESCRIPTION OF MAKING AND USING THE INVENTION

As noted above, the immunoregulatory substances of the invention include: a mixture of $F(ab')_2$ fragments (or other divalent binding molecules which lack Fc) which each bind noncompetitively to different monovalent antigenic epitopes on the same antigen; the $F(ab')_2$ fragment (or other fragments which lack Fc) of a bispecific antibody which has each of its binding sites derived from one of the two MAbs that bind noncompetitively to monovalent antigenic epitopes on the same antigen; a conjugate including a polymeric backbone, such as polyethylene glycol ("PEG"), cellulose, dextran, agarose, or an amino acid copolymer or a liposome, that is coupled with binding molecules, e.g., Fv, Fab, or $F(ab')_2$, which bind noncompetitively to monovalent antigenic epitopes on the same antigen.

The Fv fragments of the MAbs may be produced in bacteria using single chain antibody technology, as described in U.S. Pat. No. 4,946,778 and International Application No. WO88/09344. The Fv may also be genetically engineered to contain glycosylation sites and produced in mammalian cells, to result in a fragment containing carbohydrate moieties.

The Fab or $F(ab')_2$ may be produced by enzymatic cleavage of whole IgG which is produced by a hybridoma or a transfected cell lines (a myeloma or a cell line such as CHO), using pepsin and papain digestion, respectively.

The Fab or $F(ab')_2$ fragments may be wholly animal or human derived, or they may be in chimeric form, such that the constant domains are derived from the constant regions of human immunoglobulins and the variable regions are derived from the parent murine MAb. Alternatively, the Fv, Fab, or $F(ab')_2$ may be humanized, so that only the complementarity determining regions (CDR) are derived from an animal MAb, and the constant domains and the framework regions of the variable regions are of human origin. These chimeric and humanized fragments are less immunogenic than their wholly animal counterparts, and thus more suitable for in vivo use, especially over prolonged periods.

Methods of making chimeric and humanized antibodies are well known in the art, (see, e.g., U.S. Pat. No. 4,816,567, International Application No. WO84/03712, respectively). The Fv, Fab, or F(ab')$_2$ fragments may be produced from such chimeric or humanized antibodies using proteolytic digestion, as described above.

The antibody fragments can be conjugated to the linear or cross-linked backbone of a liposome using conventional techniques. See, e.g. Ostro, M. J. (Ed.), *Liposomes: from Biophysics to Therapeutics* (Marcel Dekker, New York, 1987). One preferred method of preparing liposomes and conjugating immunoglobulins to their surface is described by Ishimoto, Y. et al., *J. Immunol. Met.* 75, 351–360 (1984). Multilamillar liposomes composed of dipalmitoylphosphatidylcholine, cholesterol and phosphotidylethanolamine are prepared. Purified fragments can then be coupled to the phosphatidylethanolamine by the cross-linking agent N-hydroxysuccinimidyl 3-(2-pyridyldithio) propionate. The coupling of the fragment to the liposome can be demonstrated by the release of a pre-trapped marker, e.g., carboxyfluorescence, from the liposomes upon the treatment of secondary antibody against the conjugated fragment and complement.

The antibody fragments may also be coupled to a liposome or another carrier of the invention via their carbohydrate moieties. Provided that the carbohydrate moiety is not in the hypervariable region or at the antibody binding sites, the conjugation via the crosslinking with the carbohydrate will not affect binding, as the binding sites will still be available to bind to cell surface antigens.

One preferred way to couple fragments of the invention (other than Fv) to a polymer backbone or a liposome is to conjugate them through the carbohydrate moiety on the constant regions. This will maximize the binding sites which are available, and not hindered, for binding to the antigens.

Methods for derivatizing sugar ring moities to create hydrazide groups for coupling with fragments (and antibodies) has been established. See Rodwell, J. D. et al., *Proc. Nat'l Acad. Sci. USA* 83:2632–36 (1986). Several immunoconjugates prepared in this way are in clinical studies or pending approval for routine clinical uses.

The polymers for conjugating to the antigen binding sites can be modified to generate active groups for coupling according to established methods. For example, PEG can be derivatized by 1,1'-carbonyldiamidazole to form imidazole carbamate active groups, which react with amino groups of proteins. Beauchamp, C. O. et al., *Anal. Biochem.* 131:25 (1983). Similar reactions can be used for derivatizing agarose. Bethell, G. S. et al., *J. Biol. Chem.* 254:2572 (1979).

The antibody fragments can be coupled directly to the derivatized, activated polymers. Bifunctional cross-linkers suitable for conjugating the activated polymers (or liposomes) and the fragments, can be selected based on the properties desired and the specific substances to be cross-linked. These heterobifunctional reagents are available from several commercial sources, e.g., Pierce Chemical Co., Rockford, Ill., and the reaction procedures are well-known.

The substances of the invention, in appropriate pharmaceutical vehicles, may be administered intravenously (i.v.), so that they can reach spleen, liver, and various lymph nodes. They will also reach the T and B cells in circulation when administered i.v.

The substances of the invention may also be given intraperitoneally (i.p.), where they will mainly interact with cells in the peritoneal cavity and will be delivered to other lymphoid tissues through the lymphoid circulation. The T cells which are activated and expanded in the spleen and peritoneal cavity may also travel to different tissues in the circulation.

The substances of the invention may also be injected directly into or near the solid tumors, warts, or other affected tissues. In this case, the T cells will be activated and expanded and mediate various immune mechanisms.

Certain substances of the invention may only induce the activation of resting lymphocytes and not their proliferation. In such case, their administration may be followed by T or B cell growth factors, such as IL-2, or IL-4.

The substances of the invention may be given alone, or in combination with surgery, irradiation treatment, or chemotherapy for cancer patients, or in combination with viral antibiotics or other anti-viral substances for patients with infectious diseases. Certain of the substances of the invention, e.g., anti-mIgA, may be given as adjuvants for vaccines or infectious diseases.

There is adequate experimental support for the efficacy of the invention. As noted above, the interaction between the Fc of the anti-CD3 MAbs and the Fc receptors (FcR) on monocytes/macrophages is required both for the mitogenic effect in vitro and the ADCC effect in vivo. It was first found that the F(ab')$_2$ and Fab fragments of OKT3, which lacked Fc, were no longer mitogenic and also that whole OKT3 could not induce the T cells to proliferate if the monocytes were depleted from the mononuclear cells in culture. Van Wauwe, J. P., et al., *J. Immunol.* 124:2708 (1980); Chang, T. W., et al., *Proc. Natl. Acad. Sci. U.S.A.* 78:1805 (1981). It was then suggested that the mechanism of anti-CD3 mitogenic effect involved the interaction between the Fc of anti-CD3 and FcR on monocytes, because human serum, purified human IgG, or isolated Fc fragments could block the mitogenic effect of OKT3. Looney, R. F. and Abraham, G. N., *J. Immunol* 133:154 (1984); Chang, T. W., *Immunol. Today* (1985). Several studies also showed that the deficiency of FcR for IgG on monocytes would impair the mitogenic effects of anti-CD3, supporting the notion that Fc-FcR interaction is important for the mitogenic effects of anti-CD3. Ceuppens, J. L., et al., *J. Immunol.* 135:3882 (1982); Tax, W. J. M., et al., *Nature* 304:445 (1983); Tax, W. J. M., *J. Immunol.* 133:1185 (1984).

A few studies examined the mitogenic mechanism of anti-CD3 further. It was found that anti-human CD3 MAb densely conjugated to sepharose 4B beads and purified human IL-1 could induce the proliferation of T cells in culture in which the antigen presenting monocytes were completely depleted. It was concluded that the anti-human CD3 MAb-Sepharose 4B could activate the resting human T cells and the IL-1 was then able to initiate the synthesis of RNA, IL-2 secretion, IL-2 receptor expression, and ultimately, DNA synthesis. Williams, J. M., et al., *J. Immunol.* 135:2249 (1985). It was also reported that in the complete absence of monocytes, the T cells could be induced to proliferate by incubation in plastic culture plates coated with anti-human CD3 MAb, if soluble anti-human CD5 MAb was also provided in the culture medium. Ceuppens, J. L. and Baroja, M. L., *J. Immunol.* 137:1816 (1986). Later it was reported that the resting T cells depleted of accessory monocytes could proliferate in wells of microtiter plates coated with high concentration of anti-human CD3 (for 64.1 MAb, 40–1000 ng/ml) without the addition of IL-2 or monocytes. Geppert, T. D. and Lipsky, P. K., *J. Immunol.* 138:1660 (1987).

Based on these results, which show that the "solid-phase" anti-human CD3 can stimulate T cell activation and/or proliferation in the absence of monocytes, it is expected that anti-human CD3 MAb presented in certain appropriate soluble or suspension forms will also be mitogenic instead of being immunosuppressive in vivo. However, solid plastic sheets or Sepharose 4B beads, although suitable for in vitro use, may not be appropriate for in vivo use. These solid materials, whether deposited i.p. or by other routes, will be maintained in situ. They cannot be transported throughout the lymphoid system by the lymphoid circulation. For in vivo use, hydrophilic, soluble polymers or liposomes suitable for conjugating large numbers of anti-human CD3 MAb are preferred.

When anti-CD3 MAb molecules are conjugated to the polymer backbones or liposomes, the Fc portion of anti-CD3 MAb will be accessible to monocytes and macrophages and other cells of the RES, and hence will facilitate phagocytosis and clearance of such conjugates. To minimize such clearance and to ensure that the mitogenic effect of anti-CD3 will be the dominant effect, and that any suppressive effect mediated by ADCC and complement-mediated cytolysis will be the lessened to low levels, fragments of anti-CD3 MAbs which are devoid of the Fc domains (i.e. Fv, Fab, and F(ab')$_2$) and which do not cause the Fc-dependent ADCC and complement-mediated cytolysis, are conjugated to the polymer backbones or liposomes. The experiments with solid-phase bound anti-CD3 MAbs suggest that under certain conditions, the Fc domain of the antibody is not required in mitogenesis.

Among the surface molecules that are involved in the regulation of the activities of lymphocytes, the most important are the components or molecules associated with the TCR on T cells and mIg on B cells. These antigen receptors interact with antigens or antigen-presenting cells, and respond to antigen stimulation by causing the cell to undergo a sequence of activation, clonal expansion, and differentiation. The activation and expansion of lymphocytes consequently leads to various immune reactions and responses.

The TCR complex is very complicated and the structure is not fully characterized, despite extensive study. The information available indicates that the "complete" TCR complex contains one α chain, one β chain, one γ chain, one ε chain, one ζ chain, and a homodimer δ chain. The α and β chains are clonally different and α/β dimer is customarily referred to as the TCR. The remaining components of the TCR complex (γ, ε, ζ, and δ chains) are not polymorphic and are categorically referred to as the CD3 antigen.

It is known that T cells at different differentiation stages or with different functions express different sets of the chains. See e.g. Baniyash, M. et al., *J. Immunol.* 263:9874 (1988); Geisler, C. et al., *J. Immunol.* 145:1761 (1990). Thus, within the TCR complex on most T cells, the antigenic epitopes recognized by most MAbs are monovalent (one single epitope per complex).

It is possible that since there are two δ chains in the TCR complexes of some T cells, there may be two antigenic sites for some MAbs recognizing CD3-δ chain. Among these MAbs, some may be able to cross-link the CD3/TCR complexes. Because the δ chain is relatively small (16 Kd), only a small portion of it is exposed to the exterior surface. Some MAbs specific for the CD3-δ dimer may bind to one of the two divalent antigenic epitopes which are physically close together and preclude the binding of another anti-CD3-δ MAb at the same site. Thus, for practical purposes, this latter group of MAbs (which is likely a small group), although they also bind to divalent antigenic sites, they cannot cross-link the CD3/TCR complexes.

It has been suggested that in the mitogenesis of T cells with anti-CD3, the monocytes, through the interaction between Fc of anti-CD3 and the FcR on monocytes, can aggregate the CD3 antigen on the surface of T cells. Since CD3 is associated with the TCR, the aggregation of the TCR complexes triggers the activation and subsequent proliferation of the T cells. Some MAbs specific for the CD3-δ chain may recognize a divalent antigenic epitope and can cross-link and aggregate the CD3/TCR complexes. Most anti-CD3 MAbs are likely specific for a monovalent antigenic epitope on CD3-γ, CD3-ε, or CD3-δ, or even on CD3-δ. Thus, anti-CD3 MAb in soluble form cannot trigger activation and proliferation of T cells because the antigenic epitopes on the CD3 molecules which are recognized by anti-CD3 MAb are likely monovalent. Accordingly, the MAb or F(ab')$_2$ can bridge the surface molecules and form multiple pairs of CD3, but cannot cross-link and aggregate them. Thus, by using two or more anti-CD3 MAbs, each binding to a monovalent antigenic epitope on CD3 in a noncompetitive fashion, the CD3 antigen may be cross-linked and aggregated, and thereby, the T cells will be triggered to activate and proliferate. To avoid the cytotoxicity caused by the Fc domain of the anti-CD3 MAb, F(ab')$_2$ derived from whole IgG, or genetically engineering F(ab')$_2$, are preferred.

Figure 1:
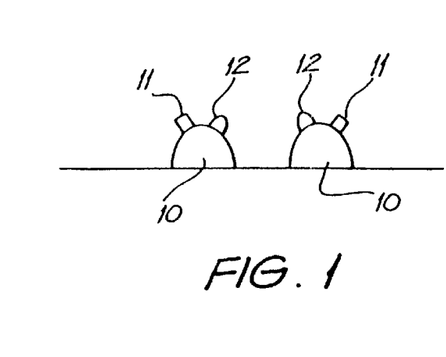
FIG. 1 A schematic representation of a surface molecule that has two monovalent antigenic epitopes, each recognized by a different MAb binding site.
Figure 2:
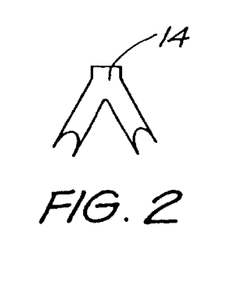
FIG. 2 A schematic illustration of a $F(ab')_2$ fragment of a MAb, which two Fab arms are identical and which is specific for one of the monovalent antigenic epitopes of the surface molecule in FIG. 1.
Figure 3:
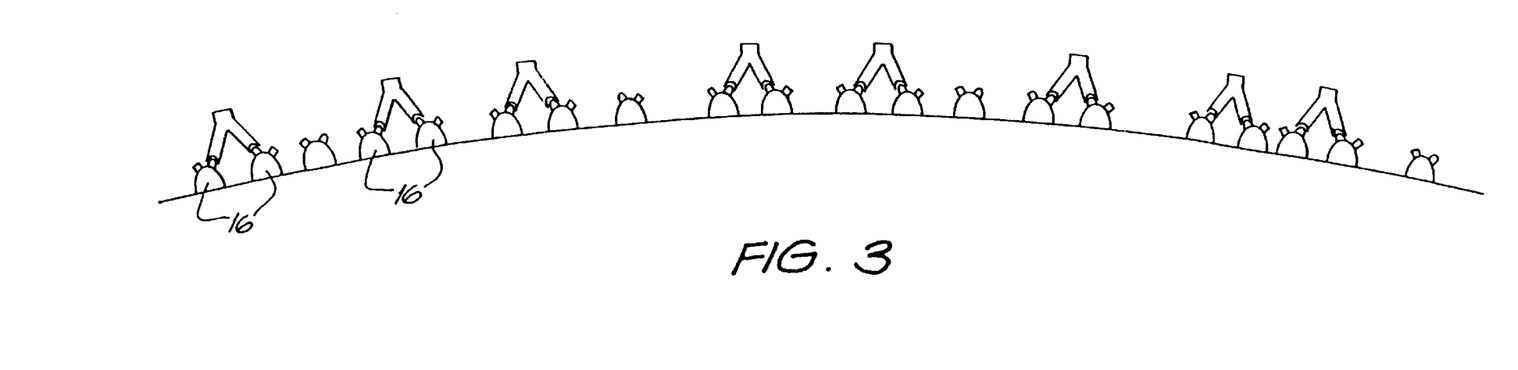
FIG. 3 A schematic representation showing the formation of pairs of molecules by the bridging of the $F(ab')_2$ of FIG. 2.

FIG. 1 schematically illustrates that a particular antigen molecule 10 contains two monovalent antigenic epitopes, 11 and 12 respectively, each recognized by one MAb fragment. FIG. 2 shows the F(ab')$_2$ of one of such MAb fragment 14. The MAb fragment 14 will cause the formation of paired antigens 16 on the surface of T cells, as shown in FIG. 3.

Figure 4:
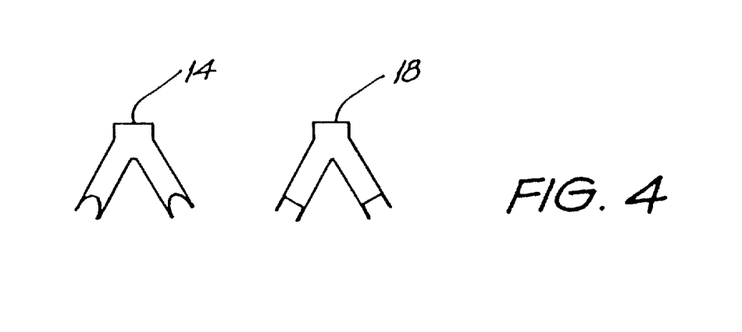
FIG. 4 A schematic representation of a mixture of two $F(ab')_2$ of two MAbs each specific for one of the monovalent antigenic epitopes of the surface molecule in FIG. 1.
Figure 5:
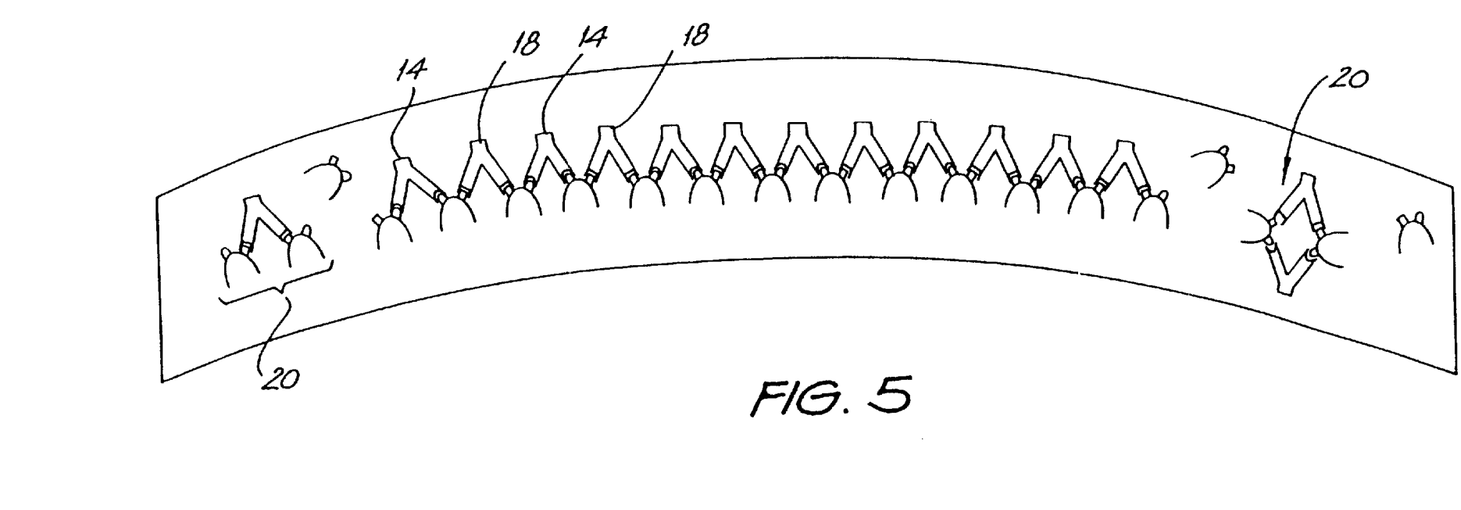
FIG. 5 A schematic representation showing the cross-linking of the surface molecules of FIG. 1 by the mixture of the two $F(ab')_2$ of FIG. 4. Note some singly-paired molecules are also formed.

To cause cross-linking and aggregation without the help of monocytes, two or more MAb fragments, each recognizing a monovalent antigenic epitope, are required. FIG. 4 schematically shows the mixture of two F(ab')$_2$ (14 and 18), each recognizing one of the two antigenic epitopes 11 and 12. FIG. 5 shows that by using the F(ab')$_2$ 14 and 18, a degree of cross-linking and aggregation can be achieved, but that some pairs of molecules 20 will also be linked. It can be appreciated that if three different anti-antigen MAbs are used, the cross-linking and aggregation will be even more pronounced.

Figures 6, 7:
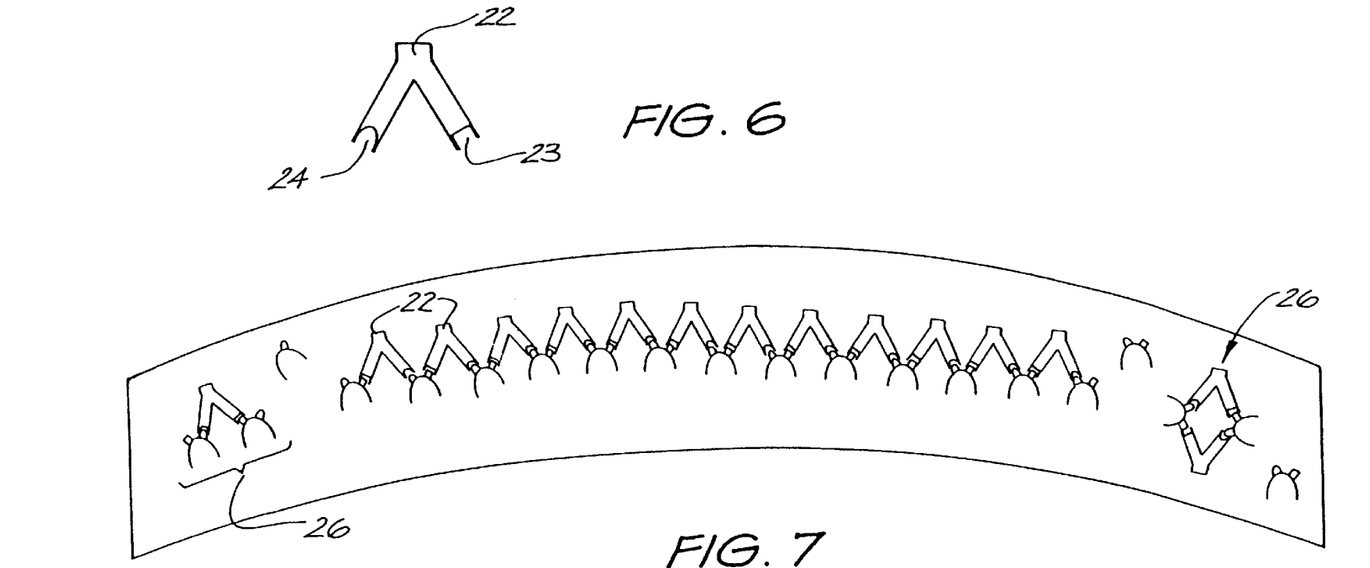
FIG. 6 A schematic representation showing a bispecific $F(ab')_2$ which is specific for both of the two different monovalent antigenic epitopes of the surface molecule of FIG. 1.
FIG. 7 A schematic representation illustrating the cross-linking of the surface epitopes of FIG. 1 by the bispecific $F(ab')_2$ of FIG. 6. Some paired molecules are formed.

FIG. 6 shows schematically a bispecific F(ab')$_2$ 22 with two specificities, 23 and 24, respectively being for the monovalent antigenic epitopes of CD3, 11 and 12. FIG. 7 shows that with this bispecific fragment 22, cross-linking and aggregation of molecules can be achieved, although some singly-paired molecules 26 are left on the T cell surface. These F(ab')$_2$ preparations will therefore also induce T cell activation and proliferation.

Another means to achieve cross-linking of antigenic epitopes on T or B cell surfaces is to use plastic sheets and Sepharose 4B beads coated or conjugated with anti-CD3 MAbs. These may be implanted or deposited into certain body sites in order to trigger mitogenesis. However, as noted above, such preparations cannot be transported through the lymphoid circulation, nor can they be administered iv. Thus, the appropriate backbone or base upon which to conjugate anti-CD3 MAb should be polymers which are hydrophilic, stable, non-immunogenic, nontoxic and resistant to hydrolases (e.g. glycosidases and proteases) in the serum and other body fluids in patients. Examples are PEG, cellulose, dextran, and agarose, which each have different molecular sizes and are all well-characterized and studied.

Another suitable "backbone" is an amino acid copolymer. One preferred amino acid copolymer includes Gly and Ser residues, and Lys, Cys, or another appropriate residue, for providing conjugation sites. Considering the molecular sizes of Fv, Fab, and F(ab')$_2$, the optimal spacing between the adjacent Lys or Cys residues is in the range of 15 to 25 amino acids. Thus, a preferred amino acid copolymer has a composition of (Gly$_{15}$Ser$_5$Lys)$_n$, where n is 5 to 600.

The fragments of the invention can also be conjugated to liposomes, using the methods described above, wherein reactive groups for cross-linking are introduced on the surface of the liposomes and the fragments are coupled thereto. For certain clinical applications with certain MAbs, fragments (or binding molecules) conjugated to liposomes may be more preferred than fragment/polymer conjugates, as the liposome conjugates can interact with antigen on T cells by a mechanism more closely resembling the interaction between cells, than when the fragment is presented on a polymer backbone.

The mitogenicity of the polymerized fragments of the invention probably depends on their sizes; more specifically, on the number of binding sites per molecular conjugate. The preferred molecular conjugates are those which are small but still are able to induce optimal mitogenic effects. Many suitable polymers are available commercially in different lengths or sizes. Amino acid copolymers of different lengths can also be synthesized and fractionated by molecular sieve chromatography. Polymers such as cellulose or agarose can be treated with specific enzymes, e.g., cellulase and agarase, to yield different lengths.

Figure 8:
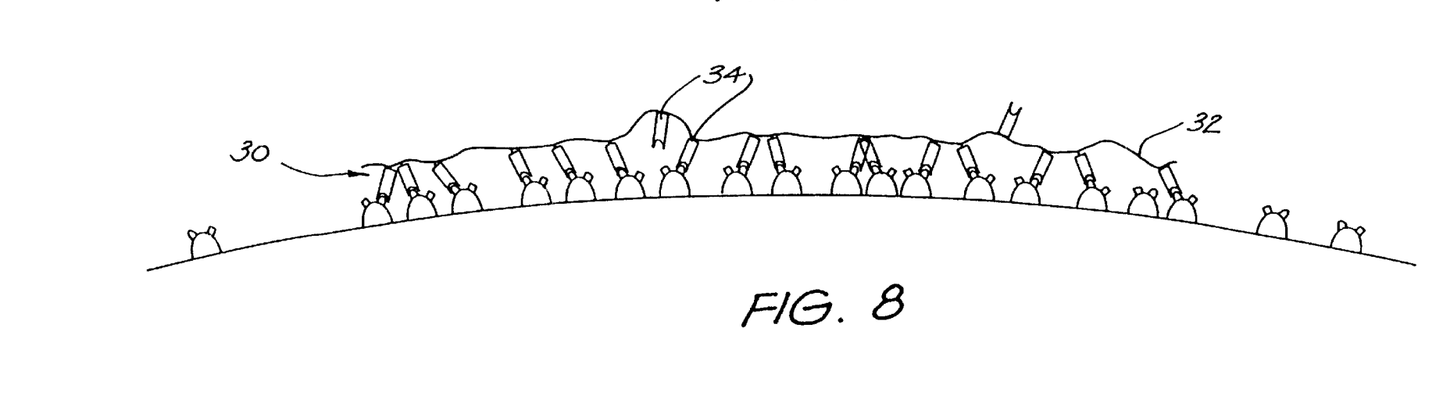
FIG. 8 A schematic representation showing the cross-linking of the surface epitopes by a monospecific polymerized MAb.

FIG. 8 schematically shows that cross-linking and aggregation of surface molecules can be achieved by using a molecular conjugate 30 consisting of a polymer backbone 32 coupled with the monovalent Fab fragment 34 specific for the monovalent antigenic epitope 12 of FIG. 1.

Figure 9:
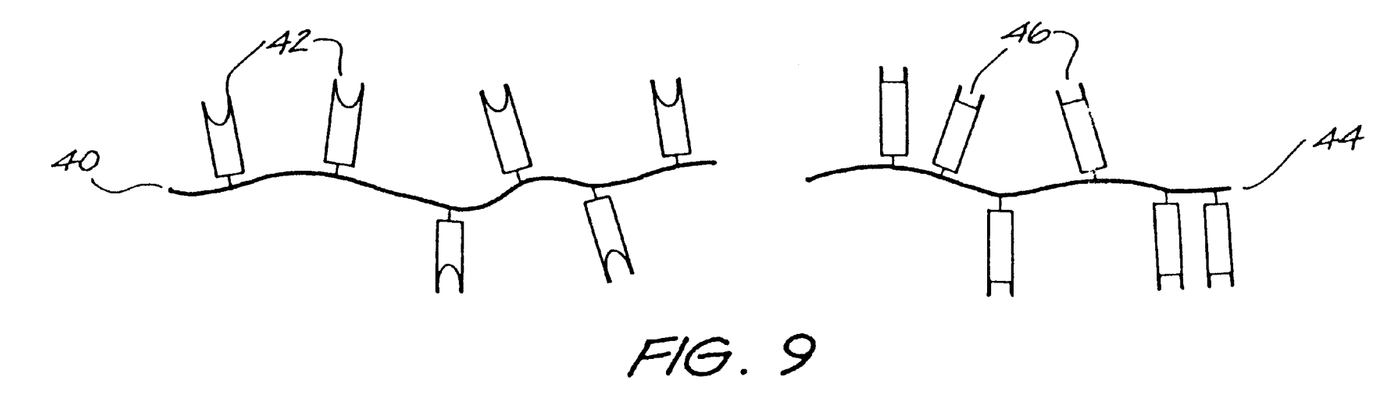
FIG. 9 A schematic representation showing the mixture of two molecular conjugates, each consisting of a polymeric backbone coupled with the Fab of a MAb specific for one of the two monovalent antigenic epitopes of the surface molecule of FIG. 1.
Figure 10:
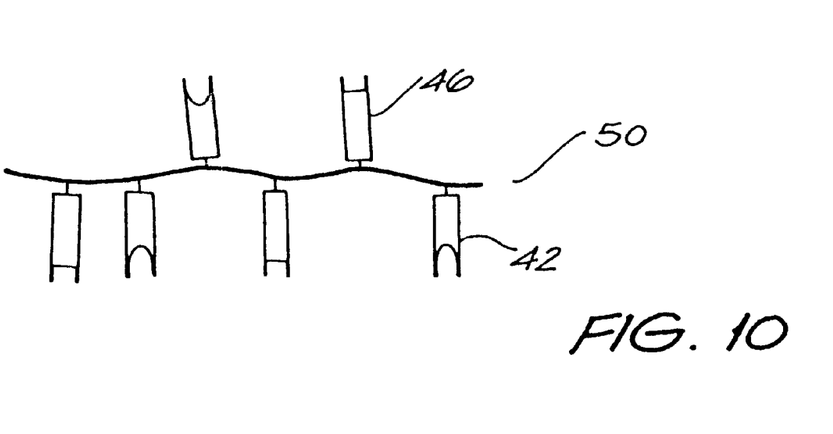
FIG. 10 A schematic representation showing the molecular conjugate of a polymeric backbone coupled with two Fab of two different MAbs, each specific for one of the two monovalent antigenic epitopes of the surface molecules of FIG. 1.

In keeping with the notion that smaller molecular conjugates are preferred provided good cross-linking and aggregation can be obtained, some other embodiments, schematically shown in FIGS. 9 and 10, are also included. Referring to FIG. 9, a polymer backbone 40 is coupled with a monovalent Fab fragment 42 against antigenic epitope 12 of FIG. 1, and a polymer backbone 44 is coupled with a monovalent Fab fragment 46 against antigenic epitope 12 of FIG. 1. In FIG. 10, a polymer backbone 50 is coupled with Fab fragments 41 and 46.

These embodiments function similarly in principle to the two products shown in FIGS. 4 and 6, the difference being that there are more binding sites in the molecular conjugates than in the F(ab')$_2$ of FIGS. 4 and 6. Because of the larger numbers of binding sites, the cross-linking and aggregation will be more complete and there will be fewer singly-paired molecules, which are not cross-linked.

As noted above, the invention is not limited to anti-CD3 fragments, but also includes binding molecules, fragments (and conjugates thereof) which are specific for surface antigens of human T or B lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products result even though the in vivo effects of IgG specific for T or B cells are primarily cytolytic effects mediated by complement, ADCC, or other cytolytic mechanisms. In addition to anti-CD3, other examples of antibodies which initiate these cytolytic effects in vivo are anti-CD4, Alters, S. E., et al., *J. Immunol.* 144:4587 (1990), and MAbs against the idiotypes of surface immunoglobulin of B cells, Meeker, T. C., et al., *Blood* 65:1349 (1985). All of these antibodies cause target cell depletion in vivo.

However, anti-CD4 and antibodies against B cell antigen receptors have been found to have stimulatory effects in vitro. This indicates that, like anti-CD3, when formulated according to the invention, they would activate or modulate their respective target cells in vivo. Similarly, one would expect that MAbs specific for components associated with the mIg on B cells would also activate or modulate the target cells.

It is noted that, unlike the fragments of the invention which are mixtures of fragments binding to at least two different antigenic determinants, single MAbs which bind to monovalent antigenic determinants cannot cross-link the antigens on the cell surface. In order to stimulate cell activation and proliferation, cross-linking of the surface antigens is usually required. However, many surface molecules such as CD4 or CD8 are single polypeptide chains or are composed of different polypeptide chains, and cannot be efficiently cross-linked by a single divalent antibody recognizing monovalent antigenic epitopes.

Further, some surface antigens contain two identical polypeptide chains, e.g., surface immunoglobulins on B cells contain 2 H chains and 2 L chains. There are not always two or more antigenic determinants on these surface antigens. If the antigenic site is on the Fab domain, there will be two antigenic sites for the MAb. However, if the antigenic site is on the Fc, there may be one or two antigenic sites which can be bound by a MAb. When the antigenic epitope recognized by a MAb is conformationally formed by two H chains, for practical purposes there is only one antigenic site, because the two sites are physically so close that only one MAb molecule can bind to them. The binding of one MAb molecule to one site precludes the binding of a second MAb molecule to the other site.

Therefore, for many surface antigens, although polyclonal antibodies which recognize many different epitopes can almost always cross-link, MAbs may link two molecules but often may not cross-link and aggregate them. The conjugates of the invention, which recognize monovalent antigenic epitopes, may achieve the same cross-linking effects as polyclonal antibodies.

The fragments of the invention, which are likely to have certain immunoregulatory effects in polymerized forms in vivo, include those which are specific for CD4, CD8, components of TCR complexes, and components associated with mIg on B cells. Specific examples of such fragments are those binding to circulating IgE and membrane-bound IgE on B cells, but not to IgE bound by the high-affinity receptors on basophils and mast cells and by the low-affinity receptors on B cells, some T cells, and granulocytes. See International Application No. PCT/US88/04706; Chang, T. W., et al., *Bio/Technology* 8:122 (1990). Other examples are fragments binding to the extracellular portion of the membrane anchor peptide of membrane-bound heavy chains of an isotype on B cells, but not to the circulating immunoglobulins of the same isotype. See International Application No. PCT/US90/05229; Davis, F. M., et al., *Bio/Technology* 9:53 (1991). Fragments binding to a surface antigen which is expressed by only lymphocytes, T cells, or B cells, or a subset of them, are potentially useful as in vivo immunomodulators in polymerized forms.

EXAMPLES

Testing Anti-CD3 MAbs for Noncompetitive Binding to CD3 on T cells

Various anti-CD3 MAbs can be purchased from commercial firms offering immunochemical reagents, including Ortho Diagnostic Systems, Raritan, N.J.; Becton Dickenson Immunological Reagents, Mountain View, Calif.; Coulter Diagnostics, Hialeach, Fla.; Sigma Chemical Co., St. Louis, Mo.; Boehringer Mannheim, Indianapolis, Ind.; Olympus Corp., Lake Success, N.Y. All these MAbs were developed by different groups. These firms offer anti-CD3 MAb not only in purified, plain IgG, but also in fluorescein-conjugated forms.

Additional MAbs against human CD3 can be readily prepared by hybridoma methodology as described by Kung, P. C. et al., Science 206:347 (1979). Using this method, many laboratories have developed murine anti-human CD3 MAb.

For determining whether two MAbs (or fragments) specific for human CD3 can bind to CD3-bearing T cells simultaneously, fluorescence flow cytometric analyses may be applied. For these analyses a human T cell line, such as CEM (ATCC CCL119 from the American Type Culture Collection), or peripheral blood mononuclear cells, can be used for the cell staining. The assay is to determine whether the binding of a FITC or rhodamine-labeled anti-CD3 MAb to the cells will be inhibited by the presence of varying concentrations of a second anti-CD3 MAb. The assay should also be reversed to determine whether the binding of the fluorescence-labeled second anti-CD3 is inhibited by the presence of the other anti-CD3.

If the binding of each anti-CD3 to the T cells is not signficantly affected by 5–10 fold concentrations of the other anti-CD3, it can be concluded that both anti-CD3 MAb can bind non-competitively to CD3 molecules on T cells. Additional confirming assays would measure whether the binding to T cells by the two MAbs is additive.

Animal model experiments, described below in the example, demonstrate that the conjugates of the invention are therapeutically efficacious in vivo.

Conjugates of the Invention as in vivo Immune Enhancers in an Animal Model System Conjugates of the invention were made by conjugating whole IgG molecules or F(ab')$_2$ fragments of the hamster monoclonal antibody 145-2C11, which is specific for murine CD3-$\epsilon$ chain, onto latex microbeads. The latex beads (of a uniform 2.5 $\mu$m diameter) were glutaraldehyde modified and were purchased from Interfacial Dynamics Corporation (Portland, Oreg.). These beads were already modified to contain activated groups for coupling with proteins. Suspensions of these beads could be made homogeneous and suitable for injection with gentle shaking. 5 $\mu$g of 145-2C11.IgG, or 3 $\mu$kg of 145-2C11.F(ab')$_2$, were conjugated onto 1 mg of the activated latex beads.

The constructs of 145-2C11.IgG/latex beads (abbreviated as "X.IgG/beads") and 145-2C11F(ab')$_2$/latex beads ("X.F(ab')$_2$/beads") were shown to be as effective as free 145-2C11 (abbreviated as "X.IgG") in inducing the proliferative response of mouse spleen cells in a 3-day in vitro assay. Unconjugated, plain beads and the fragment 145-2C11.F(ab') (abbreviated as "X.F(ab')$_2$") did not have significant effects on the proliferative response.

Various amounts of X.IgG/beads and X.F(ab')$_2$/beads were injected via the tail vein into adult BALB/c mice and their effects on the general physiology and the immune system of these mice were compared with those of mice injected with soluble X.IgG, X.F(ab')$_2$, and plain beads. The 65 mice receiving one injection of 4 to 16 $\mu$g of soluble X.IgG experienced a transient increase in spleen size which was evident 72 hours after the injection (day 3). By day 5, the spleens of these mice had begun to lose weight. The mice appeared feeble and lethargic as early as day 1 and lost 30 to 40% of their body weights by day 10. Ten of these 65 mice died, all within 4 days of the injection. The numbers of cells in the spleens of these mice that could be released by mechanically disrupting the spleens' connective tissue increased by 20–30% by day 3 and decreased to 40 to 60% of the normal levels by day 7. To a large extent, the decrease in the total spleen cells could be attributed to the loss of T cells, which were measured with a fluorescence flow cytometric method using a fluorescein isocyanate-labeled anti-Thy-1.2 antibody. In a normal mouse, T cells account for 25–35% of spleen cells. In the mice treated with X.IgG, T cells accounted for about 10% of the spleen cells on day 7. The T cells in the spleens of the treated mice remained at these low levels until day 10, and thereafter, increased, but still did not reach normal levels, even by day 14.

The mice that received one injection of up to 25 $\mu$g of soluble X.F(ab')$_2$ did not show signs of adverse effects. Their physical appearance was normal and their body weight was normal. None died. The total numbers of cells and the proportions of T cells in their spleens were not changed. These observations were consistent with the in vitro results that X.F(ab')$_2$ could not induce T cell activation and proliferation. Similarly, the mice that received one injection of unconjugated, plain latex beads at amounts up to 5 mg did not show any signs of abnormality.

In contrast, whole IgG or F(ab')$_2$ of 145-2C11 conjugated to latex microbeads (X.IgG/beads and X.F(ab')$_2$/beads) had the same effects as free 145-2C11.IgG (X.IgG) on stimulating the splenic T cells in the first 3 days. However, the bead conjugates had drastically different effects on the spleen T cells after day 3 and on the well being of the mice, as early as day 1. The mice receiving one intravenous injection of X.IgG/beads or X.F(ab')$_2$/beads, at up to 16 $\mu$g X.IgG and 25 $\mu$g X.F(ab'), respectively, developed an activated and expanded immune system. The spleen enlargement, as measured by weight or by the number of cells recovered from minced spleens, was noticeable by day 3, continued to increase until day 5 or day 6, and, thereafter, the spleens returned gradually to normal size by around day 10. The proportion of T cells in the spleens increased from 25–35% to 30–50%. Among these T cells, the proportions of activated T cells, as identified by the expression of interleukin-2 receptors on the cell surface using anti-CD25 and flow cytometry, increased dramatically from 4–6% to 13–21% by day 3.

All of the 123 mice injected with X.IgG/beads or X.F(ab')$_2$/beads appeared normal. Their agility was normal. They did not lose body weight in the two weeks after injection. None of them died. Pathological examinations revealed enlarged spleens and lymph nodes and no other major abnormal symptoms.

Another set of experiments were also ran in which mice were injected intravenously with 50 $\mu$g of chimeric human/mouse IgE (hu $\epsilon,\kappa$/mu $V_H$, $V_L$) from SE44 cells, alone an together with, respectively, X.IgG, and X.IgG/beads. Mice were also injected intraperitoneally with the chimeric human/mouse IgE together with complete Freund's adjuvant. As controls, beads and X.IgG/beads were also injected intravenously. The murine IgG response was then measured after 14 days.

The mice receiving the X.IgG/beads and chimeric human/mouse IgE had a much stronger IgG antibody response to human IgE than the mice which received only chimeric human/mouse IgE. The response of the mice receiving X.IgG/beads and chimeric human/mouse IgE was comparable to that of the mice receiving chimeric human/mouse IgE and complete Freund's adjuvant. Mice receiving soluble X.IgG with chimeric human/mouse IgE did not make a detectable antibody response, nor did mice receiving only the X.IgG/beads or only the beads.

In summary, these studies indicate that T cells and the immune system can be stimulated without T cell depletion in vivo by properly modified anti-CD3 antibodies.

It should be understood that the examples above are exemplary only and not limiting, and the invention is defined only by the following claims, and includes all equivalents of the claimed subject matter.

What is claimed is:

1. A pharmaceutical composition comprising a pharmaceutical vehicle and a molecular conjugate having a polymer backbone coupled with a plurality of binding molecules which lack an Fc portion and which are specific for an antigen on a T cell.

2. A pharmaceutical composition of claim 1, wherein the polymer is hydrophilic, stable, nonimmunogenic in humans, and resistant to hydrolysis in human body fluids.

3. A pharmaceutical composition of claim 1, wherein the polymer is cellulose, dextran, agarose, or an amino acid copolymer.

4. A pharmaceutical composition of claim 1, wherein the binding molecule is selected from the group consisting of Fv, Fab, and F(ab')$_2$.

5. A mixture of two or more molecular conjugates combined with a pharmaceutical vehicle, each comprising a polymer backbone coupled with a plurality of binding molecules of one class, each class being specific for different monovalent antigenic epitopes on the same antigen on T cells, and all said binding molecules lacking an Fc portion.

6. A mixture of claim 5, wherein the antigen is CD3, CD4, CD8, or a component associated with T cell antigen receptor.

7. A pharmaceutical composition comprising a pharmaceutical vehicle and a molecular conjugate having a polymer backbone coupled with a plurality of different binding molecules which each bind noncompetitively to monovalent antigenic epitopes on the same antigen on T cells, and all said binding molecules lacking an Fc portion.

8. A pharmaceutical composition of claim 7, wherein the antigen is CD3, CD4, CD8, or a component associated with the T cell antigen receptor.

* * * * *